(12) United States Patent
Vogt et al.

(10) Patent No.: US 7,989,519 B2
(45) Date of Patent: Aug. 2, 2011

(54) INITIATOR SYSTEM FOR SELF-CURING PLASTIC MATERIALS, ITS USE, AND BONE CEMENT COMPOSITIONS CONTAINING IT

(75) Inventors: Sebastian Vogt, Erfurt (DE); Hubert Buchner, Reinheim (DE)

(73) Assignee: Heraeus Medical GmbH, Wehrheim (DE)

( * ) Notice: Subject to any disclaimer, the term of this patent is extended or adjusted under 35 U.S.C. 154(b) by 290 days.

(21) Appl. No.: 12/254,541

(22) Filed: Oct. 20, 2008

(65) Prior Publication Data

US 2009/0105367 A1    Apr. 23, 2009

(30) Foreign Application Priority Data

Oct. 22, 2007   (DE) .......................... 10 2007 050 763

(51) Int. Cl.
*A61K 6/083*      (2006.01)
*C09K 3/00*       (2006.01)
(52) U.S. Cl. ................... 523/115; 523/116; 252/182.13; 252/182.15; 252/182.33
(58) Field of Classification Search .................. 523/115, 523/116; 252/182.13, 182.15, 182.33
See application file for complete search history.

(56) References Cited

U.S. PATENT DOCUMENTS

| 6,552,140 B1 | 4/2003 | Kneafsey et al. |
| 2003/0195273 A1 | 10/2003 | Mitra et al. |

FOREIGN PATENT DOCUMENTS

| DE | 19501933 A1 | 7/1996 |
| EP | 0732098 A2 | 9/1996 |
| EP | 1479364 A1 | 11/2004 |
| EP | 1 839 640 A2 * | 10/2007 |
| EP | 1754465 A1 | 10/2008 |
| GB | 2256875 A | 12/1992 |
| WO | 2007140440 A2 | 12/2007 |

OTHER PUBLICATIONS

English Language Abstract for DE 19501933, 1996.
English Language Abstract for EP 1754465, 2007.

* cited by examiner

*Primary Examiner* — Tae H Yoon
(74) *Attorney, Agent, or Firm* — Norris, McLaughlin & Marcus, P.A.

(57) ABSTRACT

An initiator system for self-curing plastic material comprises a) at least one salt of a dialklylbarbituric acid and/or an alkylcycloalkylbarbituric acid and/or alkylarylbarbituric acid and/or a cycloalkylarylbarbituric acid that is insoluble in methacrylate monomers; b) at least one heavy metal salt that is insoluble in methacrylate monomers; c) at least one halogenide ion donor that is insoluble in methacrylate monomers; and d) at least one acid that is soluble in methacrylate monomers. The initiator system can be used for the preparation of paste/paste, paste/powder, paste/liquid, powder/liquid, and liquid/liquid combinations for the production of medical plastic material and dental materials. Additionally, a bone cement composition containing the initiator system is described.

12 Claims, No Drawings

INITIATOR SYSTEM FOR SELF-CURING PLASTIC MATERIALS, ITS USE, AND BONE CEMENT COMPOSITIONS CONTAINING IT

The invention is related to an initiator system for self-curing plastic materials, its use, and bone cement compositions containing it.

Initiator systems for radical polymerisation of methacrylate monomers and other monomers that can be polymerised by radical polymerisation have been known for a long time. Accordingly, EP 0 732 098 A2 discloses a combination of peroxides and metal compounds. Here, a combination of cumene hydroperoxide, a metal compound, and thiourea is used. A similar combination of thiourea and a hydroperoxide is proposed in EP 1 479 364 A1. In contrast, DE 195 01 933 A1 discloses mixtures of hydroperoxides and siccatives. A new interesting system based on hydroperoxides, acylthioureas, and copper salts is presented in EP 1 754 465 A1. The advantage of initiator systems of this type is their high thermal stability. Hydroperoxides are irritating compounds and therefore suited only to a limited extent for initiation of PMMA bone cements, which are in direct contact with vital bone tissue. For this reason, initiation systems of this type have thus far not found widespread use for the production of PMMA bone cements.

The initiation system, dibenzoylperoxide and N,N-dimethyl-p-toluidine, that is used in current PMMA bone cements has proven its value on principle (K.-D. Kühn: Knochenzemente für die Endoprothetik: Ein aktueller Vergleich der physikalischen und chemischen Eigenschaften handelsüblicher PMMA-Zemente. Springer-Verlag Berlin Heidelberg New York, 2001). In this context, the dibenzoylperoxide is present as a solid in the cement powder and the N,N-dimethyl-p-toluidine is dissolved in the monomer component. This renders the initiation system stabile for storage at room temperature. However, this initiation system is suited only to a limited extent for the production of cement pastes since the dibenzoylperoxide dissolved in the monomer is meta-stabile and spontaneously decomposes to a small degree even at room temperature. As a result, paste-like cements utilising the dibenzoylperoxide/N,N-dimethyl-p-toluidine initiation system and monomers with a cross-linking effect tend to cross-link spontaneously and are therefore limited in terms of their stability for storage.

In dental applications, the initiation system, barbituric acid derivative/copper ions/chloride ions, has demonstrated its value, on principle, for the production of plastic materials that do not subsequently become discoloured, whereby, in general, only powder-liquid systems are sufficient stabile for storage. In pastes, the barbituric acid derivatives are dissolved in the monomers of the paste. It has been observed in this regard that spontaneous cross-linking of the pastes often occurs due to spontaneous decomposition of the dissolved initiator in case monomers with a cross-linking effect are used.

In summary, it can be said that no sufficiently stabile low-toxicity initiation system is known to date that is suited for the production of paste-like PMMA bone cements that are stabile for storage. In two-component bone cements, it is absolutely necessary to have a processing time of several minutes after mixing the two components in order to allow the total endoprostheses to be positioned correctly. No suitable initiation system is known to date that allows paste cements containing multi-functional monomers to have a processing time of several minutes.

The invention is based on the object to develop an initiator system that is suitable for the production of PMMA cement pastes that are stabile for storage, and facilitates reliable initiation of the radical polymerisation of PMMA cement pastes. The polymerisation is to be initiated with a delay by the initiation system such that a PMMA cement paste processing time of at least 2.5 minutes can be provided.

The invention is based on the observation that calcium, magnesium, and iron salts of barbituric acid derivatives and certain inorganic copper salts, such as basic copper carbonate and copper(II) hydroxide, are insoluble in common methacrylate monomers. The rationale underlying the invention is to use a combination of salts of barbituric acid derivatives that are insoluble in methacrylate monomers and heavy metal salts that are insoluble in methacrylate monomers, and, right before the desired polymerisation, convert them into soluble acid forms of barbituric acid derivatives and, in the case of heavy metal salts, into heavy metal salts that are soluble in methacrylate monomer through the action of acids that are soluble in methacrylate monomers. The release of the soluble barbituric acid derivatives and the release of the soluble heavy metal salts proceed through diffusion of the acid to the insoluble salts and then the released soluble barbituric acid derivatives and heavy metal salts diffuse towards each other. Only when these meet and chloride ions are present, radical formation, and therefore initiation of polymerisation, occurs. This means that the actual initiation step is preceded by dissolution and diffusion processes that are rate-limiting for the initiation of polymerisation.

The object of the invention was met by an initiator system for self-curing plastic materials that contains the components,
a) at least one salt of a dialkylbarbituric acid and/or an alkylcycloalkylbarbituric acid and/or alkylarylbarbituric acid and/or a cycloalkylarylbarbituric acid that is insoluble in methacrylate monomers;
b) at least one heavy metal salt that is insoluble in methacrylate monomers;
c) at least one halogenide ion donor that is soluble in methacrylate monomers; and
d) at least one acid that is soluble in methacrylate monomers.

The term, methacrylate monomer, is used in polymer chemistry to refer to common methacrylate monomers. These include methylmethacrylate, ethylmethacrylate, propylmethacrylate, butylmethacrylate, hexylmethacrylate, cyclohexylmethacrylate, octylmethacrylate, decylmethacrylate, ethylene glycol dimethacrylate, propan-1,2-diol-dimethacrylate, butan-1,4-diol-dimethacrylate, hexan-1,6-diol-dimethacrylate, octan-1,8-diol-dimethacrylate, diethylene glycol dimethacrylate, triethylene glycol dimethacrylate, tetraethylene glycol dimethacrylate. Also included in the methacrylate monomers are BisGMA and methacrylate-terminated macromers.

In this context, the components a) and b) that are suspended in a methacrylate monomer can advantageously be converted into dialkylbarbituric acid and/or alkylcycloalkylbarbituric acid and/or alkylarylbarbituric acid and/or cycloalkylarylbarbituric acid, all soluble in methacrylate monomers, and into heavy metal salts of the acid that are soluble in methacrylate monomers through the action of the acid that is soluble in methacrylate monomers.

Calcium salts, magnesium salts, and iron salts of dialkylbarbituric acids, alkylcycloalkylbarbituric acids, alkylarylbarbituric acids, and cycloalkylarylbarbituric acids are preferred.

Calcium salts of 1-cyloalkyl-5-alkylbarbituric acids and 1-phenyl-5-alkyl-barbituric acids are particularly preferred, whereby the calcium salt of 1-cyclohexyl-5-ethyl-barbituric acid is even more particularly preferred.

As heavy metal salts, copper(II) hydroxide, basic copper carbonate, iron(II) carbonate, manganese(II) carbonate, and cobalt(II) carbonate are preferred.

As halogenide ion donor(s), tetraalkylammonium chlorides are preferred according to the invention, whereby trioctylmethylammonium chloride is particularly preferred.

As acid that is soluble in methacrylate monomers, preferably 2-ethylhexanoic acid, hexanoic acid, heptanoic acid, octanoic acid, and malonic acid are conceivable. In addition, it is also feasible to use, as soluble acid, monomers with acid functions, such as sulfonic acid, phosphoric acid, phosphonic acid, and carbonic acid groups. It is also feasible to use acetic acid, propionic acid, pivalic acid, chloroacetic acid, methanesulfonic acid, and phosphoric acid. The use of acids that are soluble in methacrylate monomers and form poorly water-soluble salts with calcium ions is particularly advantageous.

A combination of the calcium salt of 1-cyclohexyl-5-ethylbarbituric acid, basic copper(II) carbonate, trioctylammonium chloride, and 2-ethyl-hexanoic acid—or a combination of the calcium salt of 1-cyclohexyl-5-ethylbarbituric acid, copper(II) hydroxide, trioctylammonium chloride, and 2-ethyl-hexanoic acid—is/are particularly preferred.

Before mixing components a), b), c), and d), components a) and b) can be dispersed in a paste or a powder or a liquid, and components c) and d) can be dispersed separately in a second paste or a powder or a liquid.

The invention is related to the use of the initiator system described above for the preparation of paste/paste, paste/powder, paste/liquid, powder/liquid, and liquid/liquid combinations for the production of medical plastic materials and dental materials.

The initiator system according to the invention is preferably contained in a bone cement composition, in which a paste-like component A, composed of at least one methacrylate monomer, at least one polymethylmethacrylate that is soluble in methacrylate monomers, one polymethylmethacrylate that is insoluble in methacrylate monomers, a salt of a dialkylbarbituric acid and/or an alkylcycloalkylbarbituric acid and/or alkylarylbarbituric acid and/or a cycloalkylarylbarbituric acid that is insoluble in the methacrylate monomer, and at least one heavy metal salt that is insoluble in methacrylate monomers, and a paste-like component B, composed of at least one methacrylate monomer, at least one polymethylmethacrylate that is soluble in methacrylate monomers, one polymethylmethacrylate that is insoluble in methacrylate monomers, a halogenide ion donor that is soluble in methacrylate monomers, and at least one acid that is soluble in methacrylate monomers, are present.

The term, polymethylmethacrylate, refers to homopolymers of methylmethacrylate and also to copolymers of methylmethacrylate and other monomers, such as methylacrylate, ethylacrylate, ethylmethacrylate, propylmethacrylate, butylacrylate, styrene, and methylstyrene.

The invention is illustrated in more detail by the examples presented below without limiting the scope of the invention. Like in all parts of the description, specification of parts and percentages refers to the weight unless specified otherwise.

EXAMPLE 1

Synthesis of the Calcium Salt of
1-cyclohexyl-5-ethyl-barbituric Acid (CaCHEBA)

A total of 10.000 g (42 mmol) 1-cyclohexyl-5-ethyl-barbituric acid and 1.621 g (21 mmol) calcium hydroxide were suspended in 50 ml methanol under stirring. Subsequently, stirring was continued for one hour at room temperature. Then, the methanol was removed using a vacuum rotary evaporator and the remaining residue was dried in a vacuum without any further cleaning operations until the mass was constant, whereby a colourless solid was obtained.

Yield: 11.000 g (97.8%)

FT-IR $\tilde{\nu}$ (cm$^{-1}$): 3211; 3134; 3083; 2940; 2857; 1748; 1711; 1664; 1427; 1364; 1319; 1260; 1207; 1136; 1088; 1075; 1043; 998; 896; 858; 805; 768; 754; 736; 717; 666.

EXAMPLE 2

Production of a Mixture of Zirconium Dioxide and Copper Carbonate

A total of 20.000 g zirconium dioxide powder were mixed with 40 mg basic copper(II) carbonate ($CuCO_3 \cdot xCu(OH)_2$) by intensive grinding.

EXAMPLE 3

Production of a Mixture of Zirconium Dioxide and Copper Carbonate

A total of 10.000 g zirconium dioxide powder were mixed with 20 mg copper(II) hydroxide (stabilised $Cu(OH)_2$) by intensive grinding.

EXAMPLE 4

Production of a Polymer Solution 1

A total of 15.0 g poly-methylmethacrylate-co-methylacrylate (molecular mass approx. 600,000; approx. 50% methylacrylate fraction) were dissolved in 85.0 g hexan-1,6-diol-dimethacrylate at room temperature under intensive stirring. A viscous, clear solution was produced in the process.

EXAMPLE 5

Production of a Polymer Solution 2

A total of 10.0 g poly-methylmethacrylate-co-methylacrylate (molecular mass approx. 600,000; approx. 50% methylacrylate fraction) were dissolved in 90.0 g Hexan-1,6-diol-dimethacrylate at room temperature under intensive stirring. A viscous, clear solution was formed in the process.

A particulate poly-methylmethacrylate-co-methylacrylate (molecular mass approx. 800,000; approx. 50% methylacrylate fraction, grain size <63 μm), hereinafter called polymer 1, was used for the pastes described in the following in examples 6-13.

EXAMPLE 6

Paste 1

Pastes A and B were produced by simple kneading. Paste A and paste B were brush-applicable, visually homogeneous pastes that could be mixed with each other without difficulty.

|  | Composition | |
|---|---|---|
| Paste components | Paste A | Paste B |
| Polymer 1 | 4.998 g | 5.250 g |
| Polymer solution 1 | 3.500 g | 3.500 g |
| Mixture of zirconium dioxide and copper carbonate | 1.002 g | — |
| Zirconium dioxide | — | 1.000 g |
| CaCHEBA | 0.500 g | |
| 2-Ethyl-hexanoic acid | — | 0.200 g |
| ALIQUAT 336 | — | 0.050 g |

The paste generated after mixing of components A and B was easy to shape and apply with a brush without difficulty. The curing started 2 minutes and 50 seconds after the mixing.

EXAMPLE 7

Paste 2

|  | Composition | |
|---|---|---|
| Paste components | Paste A | Paste B |
| Polymer 1 | 4.998 g | 5.250 g |
| Polymer solution 1 | 3.500 g | 3.500 g |
| Mixture of zirconium dioxide and copper carbonate | 0.501 g | — |
| Zirconium dioxide | 0.501 g | 1.000 g |
| CaCHEBA | 0.500 g | |
| 2-Ethyl-hexanoic acid | — | 0.200 g |
| ALIQUAT 336 | — | 0.050 g |

The curing started 4 minutes and 10 seconds after the mixing of components A and B.

EXAMPLE 8

Paste 3

|  | Composition | |
|---|---|---|
| Paste components | Paste A | Paste B |
| Polymer 1 | 4.998 g | 5.250 g |
| Polymer solution 1 | 3.500 g | 3.500 g |
| Mixture of zirconium dioxide and copper carbonate | 0.250 g | — |
| Zirconium dioxide | 0.752 g | 1.000 g |
| CaCHEBA | 0.500 g | |
| 2-Ethyl-hexanoic acid | — | 0.200 g |
| ALIQUAT 336 | — | 0.050 g |

The curing started 6 minutes and 15 seconds after the mixing.

EXAMPLE 9

Paste 4

|  | Composition | |
|---|---|---|
| Paste components | Paste A | Paste B |
| Polymer 1 | 4.998 g | 5.250 g |
| Polymer solution 1 | 3.500 g | 3.500 g |
| Mixture of zirconium dioxide and copper carbonate | 1.002 g | — |
| Zirconium dioxide | — | 1.000 g |
| CaCHEBA | 0.500 g | |
| Octanoic acid | — | 0.200 g |
| ALIQUAT 336 | — | 0.050 g |

After mixing of components A and B, the paste again was easy to shape and apply with a brush without difficulty. The curing started 3 minutes and 5 seconds after the mixing.

EXAMPLE 10

Paste 5

|  | Composition | |
|---|---|---|
| Paste components | Paste A | Paste B |
| Polymer 1 | 4.998 g | 5.250 g |
| Polymer solution 1 | 3.500 g | 3.500 g |
| Mixture of zirconium dioxide and copper carbonate | 1.002 g | — |
| Zirconium dioxide | — | 1.000 g |
| CaCHEBA | 0.500 g | |
| Heptanoic acid | — | 0.200 g |
| ALIQUAT 336 | — | 0.050 g |

After mixing of components A and B, the paste again was easy to shape and apply with a brush without difficulty. The curing started 3 minutes and 5 seconds after the mixing.

EXAMPLE 11

Paste 6

|  | Composition | |
|---|---|---|
| Paste components | Paste A | Paste B |
| Polymer 1 | 4.998 g | 5.250 g |
| Polymer solution 1 | 3.500 g | 3.500 g |
| Mixture of zirconium dioxide and copper hydroxide | 0.501 g | — |
| Zirconium dioxide | 0.501 g | 1.000 g |
| CaCHEBA | 0.500 g | |
| Heptanoic acid | — | 0.200 g |
| ALIQUAT 336 | — | 0.050 g |

After mixing of components A and B, the paste again was easy to shape and apply with a brush without difficulty. The curing started 3 minutes and 20 seconds after the mixing.

EXAMPLE 12

Paste 7

| Paste components | Composition | |
|---|---|---|
| | Paste A | Paste B |
| Polymer | 4.998 g | 5.250 g |
| Polymer solution 2 | 3.500 g | 3.500 g |
| Mixture of zirconium dioxide and copper hydroxide | 0.501 g | — |
| Zirconium dioxide | 0.501 g | 1.000 g |
| CaCHEBA | 0.500 g | |
| 2-Ethyl-hexanoic acid | — | 0.200 g |
| ALIQUAT 336 | — | 0.050 g |

After mixing of components A and B, the paste again was easy to shape and apply with a brush without difficulty. The curing started 4 minutes and 25 seconds after the mixing.

EXAMPLE 13

Powder-liquid cement 1.50 g CaCHEBA, 6 mg basic copper(II) carbonate, 6.00 g zirconium dioxide, 6.00 g poly-methylmethacrylate-co-methylacrylate (molecular mass 600,000, approx. 50% methylacrylate), 26.50 g poly-methylmethacrylate-co-methylacrylate (molecular mass approx. 800,000; approx. 5-8% methylacrylate) were ground intensively. The monomer liquid was produced by mixing 20 ml methylmethacrylate (stabilised with 200 ppm hydroquinone) and 100 mg ALIQUAT 336 and 400 mg 2-ethyl-hexanoic acid. As a result of mixing the cement powder and the monomer liquid, a cement dough was formed that was capable of being processed for approx. 8 minutes and then cured over a period of approx. 5 minutes.

The invention claimed is:

1. An initiator system for self-curing plastic materials, comprising
    a) at least one salt of a dialkylbarbituric acid or a salt of alkylcycloalkylbarbituric acid or a salt of alkylarylbarbituric acid or a salt of a cycloalkylarylbarbituric acid, wherein said acid salt is insoluble in methacrylate monomers;
    b) at least one heavy metal salt that is insoluble in methacrylate monomers;
    c) at least one halogenide ion donor that is soluble in methacrylate monomers; and
    d) at least one acid that is soluble in methacrylate monomers,
    wherein components a) and b) are dispersed in a first paste, powder or liquid, and in that components c) and d) are dispersed separately in a second paste, powder or liquid.

2. The initiator system for self-curing plastic materials according to claim 1 wherein components a) and b) that are suspended in a methacrylate monomer can be converted into dialkylbarbituric acid and/or alkylcycloalkylbarbituric acid and/or alkylarylbarbituric acid and/or cycloalkylarylbarbituric acid, all soluble in methacrylate monomers, and into heavy metal salts of the acid that are soluble in methacrylate monomers through the action of the acid that is soluble in methacrylate monomers.

3. The initiator system for self-curing plastic materials according to claim 1 wherein component a) is selected from compounds of the group consisting of calcium salts, magnesium salts, and iron salts of dialkylbarbituric acids, alkylcycloalkylbarbituric acids, alkylarylbarbituric acids, and cycloalkylarylbarbituric acids.

4. The initiator system for self-curing plastic materials according to claim 1 wherein a) is selected from the group consisting of the calcium salts of 1-cyloalkyl-5-alkylbarbituric acids and 1-phenyl-5-alkyl-barbituric acids.

5. The initiator system for self-curing plastic materials according to claim 4 wherein component a) is the calcium salt of 1-cyclohexyl-5-ethyl-barbituric acid.

6. The initiator system for self-curing plastic materials according to claim 1 wherein component b) is selected from the group consisting of copper(II) hydroxide, basic copper carbonate, iron(II) carbonate, manganese(II) carbonate, and cobalt(II) carbonate.

7. The initiator system for self-curing plastic materials according to claim 1 wherein the halogenide ion doner is tetraalkylammonium chlorides.

8. The initiator system for self-curing plastic materials according to claim 1 wherein the acid that is soluble in methacrylate monomers is selected from the group consisting of 2-ethylhexanoic acid, hexanoic acid, heptanoic acid, octanoic acid and malonic acid.

9. The initiator system for self-curing plastic materials according to claim 1 comprising a) a calcium salt of 1-cyclohexyl-5-ethylbarbituric acid, b) basic copper carbonate, c) trioctylammonium chloride, and d) 2-ethyl-hexanoic acid.

10. The initiator system for self-curing plastic materials according to claim 1 comprising a) the calcium salt of 1-cyclohexyl-5-ethylbarbituric acid, b) copper hydroxide, c) trioctylammonium chloride, and d) 2-ethyl-hexanoic acid.

11. A bone cement composition comprising a first component, comprised of at least one methacrylate monomer, at least one polymethylmethacrylate that is soluble in methacrylate monomers, one polymethylmethacrylate that is insoluble in methacrylate monomers, a salt of a dialkylbarbituric acid or an alkylcycloalkylbarbituric acid or alkylarylbarbituric acid or a cycloalkylarylbarbituric acid that is insoluble in the methacrylate monomer, and at least one heavy metal salt that is insoluble in methacrylate monomers, and a second component, comprised of at least one methacrylate monomer, at least one polymethylmethacrylate that is soluble in methacrylate monomers, one polymethylmethacrylate that is insoluble in methacrylate monomers, a halogenide ion donor that is soluble in methacrylate monomers, and at least one acid that is soluble in methacrylate monomers.

12. The initiator system according to claim 7 wherein the tetraalkylammonium chloride is trioctylmethylammonium chloride.

* * * * *